US010792009B2

United States Patent
Ohuchi et al.

(10) Patent No.: US 10,792,009 B2
(45) Date of Patent: Oct. 6, 2020

(54) ULTRASONIC DIAGNOSTIC APPARATUS, ULTRASONIC IMAGE DISPLAY APPARATUS, AND MEDICAL IMAGE DIAGNOSTIC APPARATUS

(75) Inventors: Hiroyuki Ohuchi, Otawara (JP); Yasuhiko Abe, Otawara (JP); Tetsuya Kawagishi, Nasushiobara (JP); Shinichi Hashimoto, Otawara (JP)

(73) Assignee: Canon Medical Systems Corporation, Otawara-shi (JP)

( * ) Notice: Subject to any disclaimer, the term of this patent is extended or adjusted under 35 U.S.C. 154(b) by 1198 days.

(21) Appl. No.: 12/540,135

(22) Filed: Aug. 12, 2009

(65) Prior Publication Data
US 2010/0041992 A1    Feb. 18, 2010

(30) Foreign Application Priority Data

Aug. 13, 2008  (JP) ................................ 2008-208633

(51) Int. Cl.
| | | |
|---|---|---|
| *A61B 8/08* | (2006.01) | |
| *A61B 8/00* | (2006.01) | |
| *A61B 6/00* | (2006.01) | |

(52) U.S. Cl.
CPC .............. *A61B 8/08* (2013.01); *A61B 8/0883* (2013.01); *A61B 8/463* (2013.01); *A61B 8/483* (2013.01); *A61B 6/503* (2013.01); *A61B 8/0858* (2013.01)

(58) Field of Classification Search
CPC ........... A61B 6/00; A61B 8/00; A61B 8/0883; A61B 8/463
See application file for complete search history.

(56) References Cited

U.S. PATENT DOCUMENTS

| | | | | |
|---|---|---|---|---|
| 6,322,505 B1* | 11/2001 | Hossack et al. | ............. | 600/437 |
| 6,352,511 B1* | 3/2002 | Hossack et al. | ............. | 600/443 |

(Continued)

FOREIGN PATENT DOCUMENTS

| | | |
|---|---|---|
| CN | 101152096 A | 4/2008 |
| JP | 4-158855 | 6/1992 |

(Continued)

OTHER PUBLICATIONS

Kuo et al., Left ventricular wall motion analysis using real-time three-dimensional ultrasound, Ultrasound in Medicine & Biology, vol. 31, Issue 2, Feb. 2005, pp. 203-211.*

(Continued)

*Primary Examiner* — Serkan Akar
(74) *Attorney, Agent, or Firm* — Oblon, McClelland, Maier & Neustadt, L.L.P.

(57) ABSTRACT

When displaying a plurality of images in different conformations in relation to information of a tissue motion typified by a heart wall motion, support information which is used to rapidly and easily visually confirm a relative positional correspondence relationship between an MPR image, a polar mapping image, and a three-dimensional image is generated and displayed. A marker indicative of a desired local position is set and displayed as required. Further, a position corresponding to the set or changed marker may not be present on the MPR image. In such a case, the MPR image always including a position corresponding to the set or changed marker is generated and displayed by automatically adjusting a position of an MPR cross section.

21 Claims, 5 Drawing Sheets

(56) References Cited

U.S. PATENT DOCUMENTS

| | | | |
|---|---|---|---|
| 2002/0072671 A1* | 6/2002 | Chenal | A61B 6/463 600/450 |
| 2004/0002641 A1* | 1/2004 | Sjogren et al. | 600/407 |
| 2006/0045328 A1* | 3/2006 | Jacob | G06T 11/206 382/154 |
| 2006/0239527 A1* | 10/2006 | Krishnan et al. | 382/128 |
| 2007/0038087 A1* | 2/2007 | Abe et al. | 600/437 |
| 2007/0258632 A1* | 11/2007 | Friedman | A61B 8/08 382/128 |
| 2008/0008366 A1 | 1/2008 | Desh et al. | |
| 2008/0009722 A1* | 1/2008 | Simopoulos et al. | 600/437 |
| 2008/0077013 A1* | 3/2008 | Kawagishi et al. | 600/443 |
| 2008/0089571 A1* | 4/2008 | Kurita | A61B 8/08 382/131 |
| 2008/0132788 A1 | 6/2008 | Schreckenberg et al. | |
| 2008/0240494 A1* | 10/2008 | Oosawa et al. | 382/100 |
| 2008/0267482 A1* | 10/2008 | Abe | A61B 8/08 382/131 |
| 2008/0304730 A1* | 12/2008 | Abe | 382/131 |
| 2008/0317316 A1* | 12/2008 | Ohuchi et al. | 382/131 |
| 2009/0143677 A1* | 6/2009 | Govari et al. | 600/439 |
| 2009/0161938 A1* | 6/2009 | Shekhar | A61B 8/0883 382/131 |
| 2009/0198133 A1 | 8/2009 | Kawagishi et al. | |
| 2009/0270732 A1* | 10/2009 | Abe et al. | 600/443 |
| 2010/0041992 A1* | 2/2010 | Ohuchi et al. | 600/443 |
| 2010/0195887 A1* | 8/2010 | Abe et al. | 382/131 |
| 2010/0215225 A1* | 8/2010 | Kadomura | G06T 7/0012 382/128 |
| 2011/0137158 A1* | 6/2011 | Sumanaweera et al. | 600/427 |
| 2011/0190634 A1* | 8/2011 | Kawagishi et al. | 600/443 |

FOREIGN PATENT DOCUMENTS

| | | |
|---|---|---|
| JP | 11-506628 | 6/1999 |
| JP | 2001-128975 | 5/2001 |
| JP | 2005-95278 | 4/2005 |
| JP | 2007-44499 | 2/2007 |
| JP | 2007-319467 | 12/2007 |

OTHER PUBLICATIONS

U.S. Appl. No. 12/487,399, filed Jun. 18, 2009, Yasuhiko Abe, et al.
U.S. Appl. No. 12/302,506, filed Nov. 26, 2008, 2009/0198133 A1, Tetsuya Kawagishi, et al.
U.S. Appl. No. 12/109,805, filed Apr. 25, 2008, 2008/0267482 A1, Yasuhiko Abe, et al.
Office Action dated Jan. 31, 2011 in the corresponding China Application No. 200910165788.0 (with English Translation).
Office Action dated Apr. 2, 2013 in Japanese Application No. 2008-208633 (With English Translation).
Tetsuya Kawagishi, "Advanced Wall Movement Analysis Technique of Atrida™", Innervision, vol. 23, No. 5, May 2008, separate-volume supplement, pp. 6-11.

* cited by examiner

ULTRASONIC DIAGNOSTIC APPARATUS, ULTRASONIC IMAGE DISPLAY APPARATUS, AND MEDICAL IMAGE DIAGNOSTIC APPARATUS

CROSS-REFERENCE TO RELATED APPLICATIONS

This application is based upon and claims the benefit of priority from prior Japanese Patent Application No. 2008-208633, filed Aug. 13, 2008, the entire contents of which are incorporated herein by reference.

BACKGROUND OF THE INVENTION

1. Field of the Invention

The present invention relates to an ultrasonic diagnostic apparatus, an ultrasonic image display apparatus, and a medical image diagnostic apparatus that can generate and display an image concerning information of a tissue motion typified by a heart wall motion.

2. Description of the Related Art

In an ultrasonic diagnosis, how a heart beats or how a fetus moves can be displayed in real time by a simple operation, i.e., just applying an ultrasonic probe from a body surface, and examination can be repeatedly performed because of high safety. Besides, a scale of a system is smaller than that of any other diagnostic device using an X-ray, CT, or MRI, examination can be readily carried out even though the system is moved to the beside, and hence it can be said that the ultrasonic diagnosis is a convenient diagnostic technique. Although an ultrasonic diagnostic apparatus used in this ultrasonic diagnosis varies in many ways depending on types of functions provided thereto, when it comes to a small type, an ultrasonic diagnostic apparatus which can be carried with one hand has been developed. The ultrasonic diagnosis has no influence of radiation exposure as different from an X-ray, and it can be used in, e.g., obstetrics or home medical care.

There is a technology that uses such an ultrasonic diagnostic apparatus to generate and display a moving image concerning motion information of a cardiac tissue such as disclosed in, e.g., JP-A 2007-044499 (KOKAI). According to this technology, for example, a probe (an oscillating probe) that performs ultrasonic scan by oscillating a plurality of ultrasonic transducers aligned in a line or a probe having a plurality of ultrasonic transducers arranged in a two-dimensional matrix form is used to acquire time-series volume data of a heart. Further, pattern matching or the like is utilized with respect to the acquired time-series volume data to track a local region of a cardiac muscle, tissue motion information (e.g., a movement vector or strain of the cardiac muscle) is calculated from a tracking result, and this information is superimposed on a corresponding position of an MPR image, a polar map image, or a three-dimensional image (e.g., a volume rendering image) reconfigured from the volume data of the heart to display a moving image. A doctor can observe a moving state of the tissue motion of the heart by watching, e.g., the multiplanar reconstruction (MPR) image which is displayed like a moving image.

However, the technique for displaying an image concerning the tissue motion information using the conventional ultrasonic diagnostic apparatus has the following problem.

That is, in an MPR image, a polar map image, and a three-dimensional image, a positional correspondence relationship is difficult to understand. For example, it is not easy to determine a position on an MPR image or a three-dimensional image to which an arbitrary position on a polar map image corresponds. Further, a predetermined position on a polar map image may not be present on a currently displayed MPR image in some cases. Grasping a relative positional relationship between a plurality of images in such a case involves a further serious difficulty.

BRIEF SUMMARY OF THE INVENTION

In view of the above-described problem, it is an object of the present invention to provide an ultrasonic diagnostic apparatus, an ultrasonic image display apparatus, and a medical image diagnostic apparatus which can rapidly and easily visually confirm a relative positional correspondence relationship between a plurality of images when displaying the plurality of images having different conformations in relation to information of a tissue motion typified by a heart wall motion.

According to an aspect of the present invention, there is provided that an ultrasonic diagnostic apparatus comprising: a motion information generation unit which generates tissue motion information over a predetermined period by using volume data at a plurality of times which are collected over the predetermined period in relation to a tissue; an image generation unit which generates a plurality of images in different display conformations having the tissue motion information mapped thereon and support information indicative of a positional correspondence relationship between the plurality of images by using the volume data at the plurality of times and the tissue motion information over the predetermined period; and a display unit which displays the plurality of images and the support information.

According to another aspect of the present invention, there is provided that an ultrasonic diagnostic apparatus comprising: a display unit which displays an MPR image, a polar mapping image and a three-dimensional image acquired by ultrasonic-scan of a subject; a generation unit which generates support information indicative of a positional correspondence relationship between the MPR image, the polar mapping image and the three-dimensional image; and wherein the display unit displays the support information in such a manner that the support information is superimposed on the MPR image, the polar mapping image and the three-dimensional image.

According to yet another aspect of the present invention, there is provided that an ultrasonic image display apparatus comprising: a storage unit which stores tissue motion information over a predetermined period by using a volume data at a plurality of times which are collected over the predetermined period in relation to a tissue; an image generation unit which generates a plurality of images in different display conformations having the tissue motion information mapped thereon and support information indicative of a positional correspondence relationship between the plurality of images by using the volume data at the plurality of times and the tissue motion information over the predetermined period; and a display unit which displays the plurality of images and the support information.

According to yet another aspect of the present invention, there is provided that an ultrasonic image display apparatus comprising: a generation unit which generates support information indicative of a positional correspondence relationship between an MPR image, a polar mapping image and a three-dimensional image acquired by ultrasonic-scan of a subject; and a display unit displays the support information in such a manner that the support information is superimposed on the MPR image, the polar mapping image and the three-dimensional image.

According to yet another aspect of the present invention, there is provided that a medical image diagnostic apparatus comprising: a motion information generation unit which generates tissue motion information over a predetermined period by using a volume data at a plurality of times which are collected over the predetermined period in relation to a tissue; an image generation unit which generates a plurality of images in different display conformations having the tissue motion information mapped thereon and support information indicative of a positional correspondence relationship between the plurality of images by using the volume data at the plurality of times and the tissue motion information over the predetermined period; and a display unit which displays the plurality of images and the support information.

According to yet another aspect of the present invention, there is provided that a medical image diagnostic apparatus comprising: a generation unit which generates support information indicative of a positional correspondence relationship between an MPR image, a polar mapping image and a three-dimensional image acquired by ultrasonic-scan of a subject; and a display unit displays the support information in such a manner that the support information is superimposed on the MPR image, the polar mapping image and the three-dimensional image.

According to yet another aspect of the present invention, there is provided that a display method of an ultrasonic image comprising: generating a plurality of images in different display conformations having a tissue motion information mapped thereon and support information indicative of a positional correspondence relationship between the plurality of images by using a volume data at a plurality of times which are collected over a predetermined period in relation to a tissue and tissue motion information over the predetermined period; and a display unit which displays the plurality of images and the support information.

According to yet another aspect of the present invention, there is provided that a display method of an ultrasonic image comprising: generating support information indicative of a positional correspondence relationship between an MPR image, a polar mapping image and a three-dimensional image acquired by ultrasonic-scan of a subject; and displaying the support information in such a manner that the support information is superimposed on the MPR image, the polar mapping image and the three-dimensional image.

According to yet another aspect of the present invention, there is provided that a processing method of an ultrasonic image comprising: generating tissue motion information over a predetermined period by using volume data at a plurality of times which are collected over the predetermined period in relation to a tissue; generating a plurality of images in different display conformations having the tissue motion information mapped thereon and support information indicative of a positional correspondence relationship between the plurality of images by using the volume data at the plurality of times and the tissue motion information over the predetermined period; and displaying the plurality of images and the support information.

According to yet another aspect of the present invention, there is provided that a processing method of an ultrasonic image comprising: generating support information indicative of a positional correspondence relationship between an MPR image, a polar mapping image and a three-dimensional image acquired by ultrasonic-scan of a subject; and displaying the support information in such a manner that the support information is superimposed on the MPR image, the polar mapping image and the three-dimensional image.

According to yet another aspect of the present invention, there is provided that a processing method of a medical image comprising: generating tissue motion information over a predetermined period by using volume data at a plurality of times which are collected over the predetermined period in relation to a tissue; generating a plurality of images in different display conformations having the tissue motion information mapped thereon and support information indicative of a positional correspondence relationship between the plurality of images by using the volume data at the plurality of times and the tissue motion information over the predetermined period; and displaying the plurality of images and the support information.

According to yet another aspect of the present invention, there is provided that a processing method of a medical image comprising: generating support information indicative of a positional correspondence relationship between an MPR image, a polar mapping image and a three-dimensional image acquired by imaging of a subject; and displaying the support information in such a manner that the support information is superimposed on the MPR image, the polar mapping image and the three-dimensional image.

According to yet another aspect of the present invention, there is provided that a display method of a medical image comprising: generating a plurality of images in different display conformations having a tissue motion information mapped thereon and support information indicative of a positional correspondence relationship between the plurality of images by using a volume data at a plurality of times which are collected over a predetermined period in relation to a tissue and tissue motion information over the predetermined period; and a display unit which displays the plurality of images and the support information.

According to yet another aspect of the present invention, there is provided that a display method of a medical image comprising: generating support information indicative of a positional correspondence relationship between an MPR image, a polar mapping image and a three-dimensional image acquired by imaging of a subject; and displaying the support information in such a manner that the support information is superimposed on the MPR image, the polar mapping image and the three-dimensional image.

DETAILED DESCRIPTION OF THE INVENTION

A first embodiment and a second embodiment according to the present invention will now be described hereinafter with reference to the accompanying drawings. It is to be noted that like reference numerals denote constituent elements having substantially the same functions and configurations and a tautological explanation will be given only when required.

Further, the technical concept of the present invention can be applied to all of a medical image diagnostic apparatus (e.g., an ultrasonic diagnostic apparatus, an X-ray computed tomographic apparatus, a magnetic resonance imaging apparatus, or a nuclear magnetic resonance apparatus (PET or SPECT)) and a medical image processing apparatus which uses image data acquired by the medical image diagnostic apparatus to execute image processing/image display posteriori. Each of the following first and second embodiments takes a situation where the technical concept of the present invention is applied to an ultrasonic diagnostic apparatus as an example to give a specific description.

First Embodiment

Figure 1:
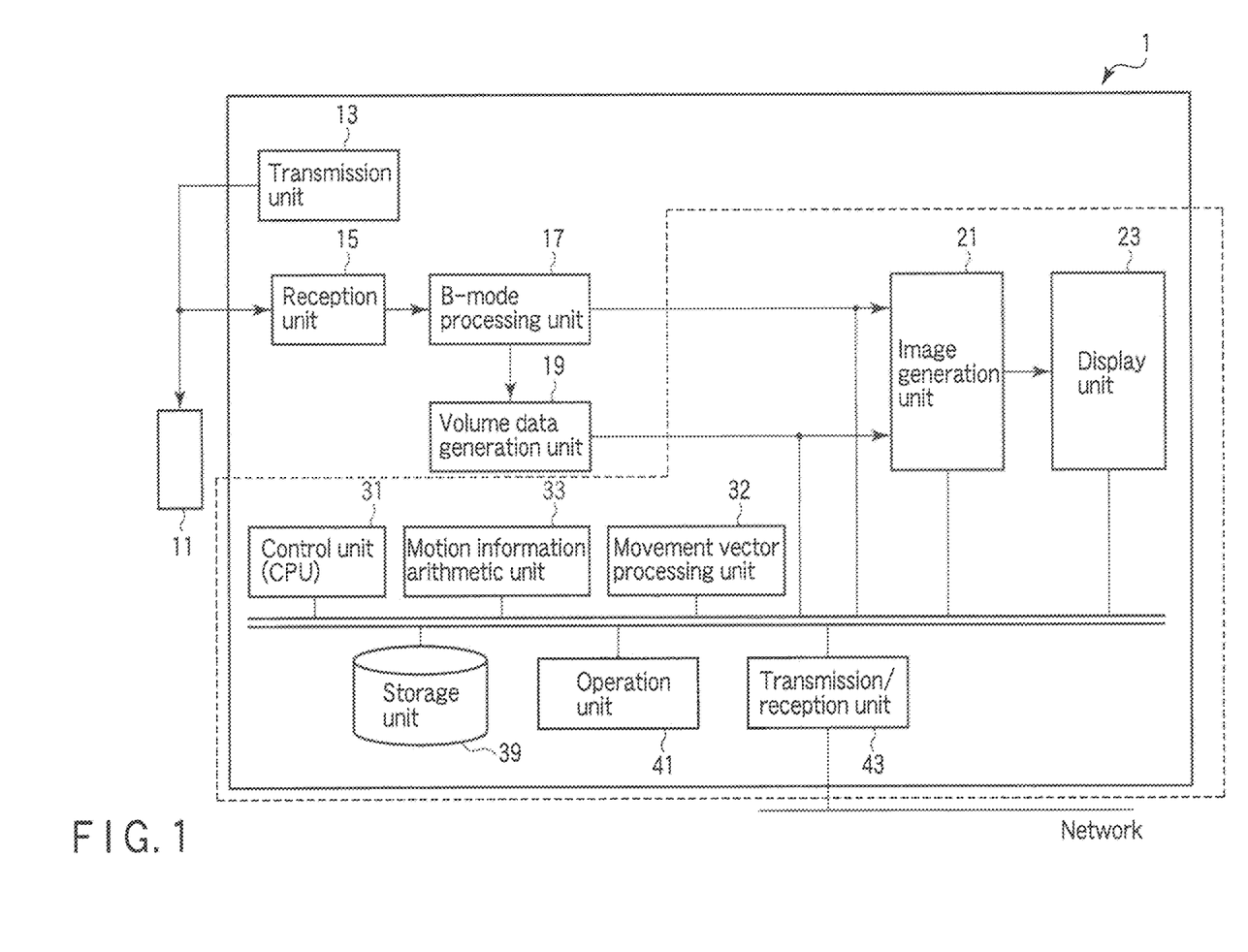
FIG. 1 is a block diagram of an ultrasonic diagnostic apparatus 1 according to a first embodiment.

FIG. 1 is a block diagram of an ultrasonic diagnostic apparatus 1 according to the first embodiment. This ultrasonic diagnostic apparatus 10 includes an ultrasonic probe 11, a transmission unit 13, a reception unit 15, a B-mode processing unit 17, a volume data generation unit 19, an image generation unit 21, a display unit 23, a control unit (a CPU) 31, a movement vector processing unit 32, a motion information arithmetic unit 33, a storage unit 39, an operation unit 41, and a transmission/reception unit 43. It is to be noted that, when applying the present invention to an ultrasonic image display apparatus, the inside of a dotted line in FIG. 1 corresponds to constituent elements.

The ultrasonic probe 11 has a plurality of piezoelectric vibrators which generate ultrasonic waves based on a driving signal from the transmission unit 13 and convert reflected waves from a subject into electric signals, a matching layer provided to the piezoelectric vibrators, a backing material which prevents ultrasonic waves from being propagated backward from the piezoelectric vibrators. When ultrasonic waves are transmitted to the subject from the ultrasonic probe 11, various harmonic components are generated with propagation of the ultrasonic waves due to, e.g., non-linearity of a living tissue. A fundamental wave and the harmonic components constituting the transmission ultrasonic waves are backscattered due to, e.g., a boundary or micro scattering of an acoustic impedance of a body tissue and received by the ultrasonic probe 11 as reflected waves (echoes).

The transmission unit 13 has a non-illustrated delay circuit, a pulsar circuit, and others. In the pulsar circuit, a rate pulse required to form the transmission ultrasonic wave is repeatedly generated with a predetermined rate frequency fr Hz (a cycle; 1/fr second). Furthermore, the delay circuit gives a delay time required to converge the ultrasonic waves in the form of a beam and determine transmission directional characteristics in accordance with each channel to each rate pulse. The transmission unit 13 applies a driving pulse in accordance with each vibrator at a timing based on this rate pulse so that an ultrasonic beam can be formed toward a predetermined scan line.

The reception unit 15 has a non-illustrated amplification circuit, an A/D converter, an adder, and others. The amplification circuit amplifies an echo signal fetched through the probe 11 in accordance with each channel. The A/D converter gives a delay time required to determine reception directional characteristics with respect to the amplified echo signal and then executes addition processing in the adder. Based on this addition, an ultrasonic echo signal associated with a predetermined scan line is generated.

The B-mode processing unit 17 performs envelope detection processing with respect to the ultrasonic echo signal received from the reception unit 15 to generate the B-mode signal associated with an amplification intensity of the ultrasonic echo.

The volume data generation unit 19 uses ultrasonic image data in each time phase concerning a predetermined region of the subject obtained by oscillating scan or three-dimensional scan to generate volume data associated with each time phase. It is to be noted that the volume data is defined as a set of reception signals having three-dimensional positional information (i.e., a set of reception signals having spatial information) in this example.

The image generation unit 21 generates a B-mode ultrasonic image representing a two-dimensional distribution concerning a predetermined cross section of a B-mode signal. Moreover, the image generation unit 21 maps calculated tissue motion information onto various kinds of images based on, e.g., volume rendering, surface rendering, polar mapping, or MPR processing to generate a two-dimensional image or a three-dimensional image concerning the tissue motion information. Additionally, when displaying a plurality of images having different conformations, the image generation unit 21 generates support information which facilitates grasping a positional correspondence relationship between the images and displays this information together with the various images.

The display unit 23 displays the tissue motion information or the like in a predetermined conformation as an image based on a video signal from the image generation unit 21 as will be described later. Further, when displaying a plurality of images, the display unit 23 displays a marker that supports associating positions of the images with each other.

The control unit (the CPU) 31 has a function as an information processor (a computer) and statically or dynamically controls operations of the ultrasonic diagnostic apparatus main body. In particular, the control unit 31 expands in a non-illustrated memory a dedicated program stored in the storage unit 39 to realize a later-explained tissue motion information display function.

The movement vector processing unit 32 tracks a movement position of a tissue by using pattern matching processing between two pieces of volume data having different time phases and thereby obtains a distance (or a velocity) of each tissue based on the acquired movement position in each time phase. Specifically, in regard to a region of interest in one volume data, a corresponding region in the other volume data having the highest similarity is obtained. Acquiring a distance between this region of interest and the corresponding region enables obtaining a distance of the tissue. Further, dividing this distance by a time difference between the volumes enables acquiring a movement velocity of the tissue. When this processing is executed at each position on the volumes in accordance with each volume, displacement (a movement vector) of each tissue or a space-time distribution data concerning the displacement of each tissue can be acquired.

The motion information arithmetic unit 33 generates a tissue motion information in accordance with each time phase based on the space-time distribution data output from the movement vector processing unit 32. Here, the tissue motion information means physical information that can be acquired in relation to, e.g., displacement, a displacement rate, strain, a strain rate, a moving distance, a velocity, a velocity gradient, and any other tissue motion concerning a predetermined direction of a predetermined tissue such as a heart wall.

The storage unit 39 is formed of a recording medium such as a magnetic disk (e.g., a floppy (a registered trademark) disk or a hard disk), an optical disk (e.g., a CD-ROM or a DVD), or a semiconductor memory and a device which reads information stored in such a medium. This storage unit 37 stores transmission/reception conditions, a predetermined scan sequence, raw data or ultrasonic image data associated with each time phase (e.g., tissue image data acquired in, e.g., a tissue Doppler mode or a B-mode), volume data previously generated in accordance with each time phase, space-time distribution data concerning a movement vector, a program which realizes a later-explained tissue motion information display function, diagnostic information (a patient ID, doctor's remarks, and others), a diagnostic protocol, a body mark generation program, and others.

The operation unit 41 is connected with the apparatus main body and has a mouse, a trackball, a mode changeover switch, a keyboard, and others which are used to input various kinds of instructions from an operator, an instruction for setting a region of interest (ROI), and an instruction for setting various image quality conditions, or select a position at which a marker is set in the later-explained tissue motion information display function, for example.

The transmission/reception unit 43 is a device which performs transmission/reception of information with any other device through a network. Data such as an ultrasonic image or an analysis result obtained in this ultrasonic diagnostic apparatus 1 can be transferred to other devices through the network by the transmission/reception unit 43.

(Tissue Motion Information Display Function)

The tissue motion information display function of this ultrasonic diagnostic apparatus 1 will now be described. When displaying a plurality of images having different conformations in relation to information of a tissue motion typified by a heart wall motion, this function generates and displays support information required to rapidly and readily visually confirm a relative positional correspondence relationship between an MPR image, a polar map image, and a three-dimensional image (e.g., a volume rendering image, or a surface rendering image). It is to be noted that a situation where the information of a tissue motion as a diagnosis target corresponds to a heart wall motion will be taken as an example in order to give a concrete description. However, it is needless to say that a target of this tissue motion information motion display function is not restricted to the heart wall motion.

Figure 2:
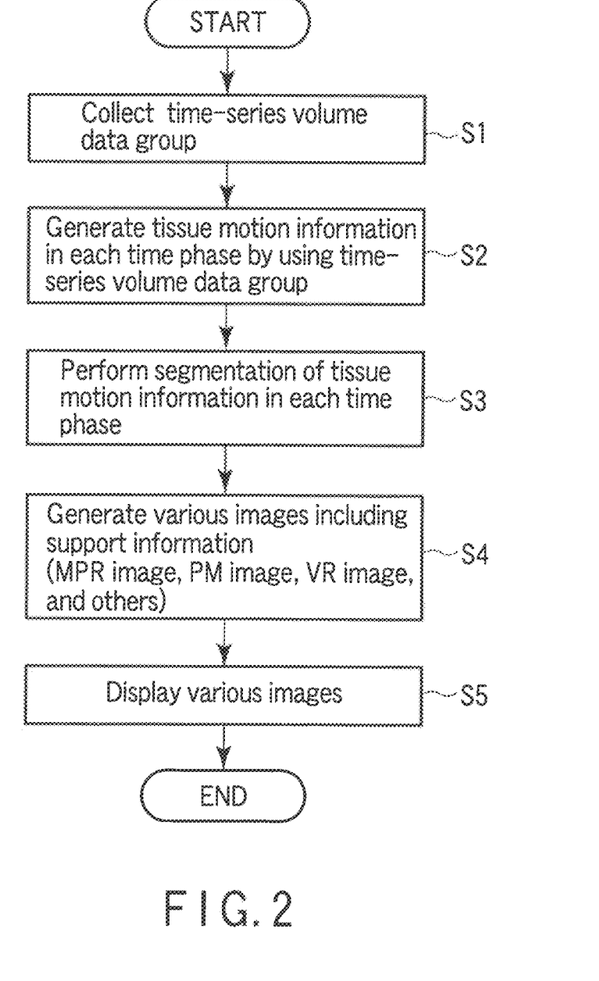
FIG. 2 is a flowchart showing a flow of each processing executed in processing according to a tissue motion information display function (a tissue motion information display processing)

FIG. 2 is a flowchart showing a flow of each processing executed in processing based on the tissue motion information display function (a tissue motion information display processing) according to this embodiment. Each processing will now be described hereinafter.

[Collection of Time-Series Volume Data: Step S1]

First, volume data in time series (which will be referred to as a "time-series volume data group" hereinafter) over a period corresponding to at least one heart beat is collected with respect to, e.g., a desired observation region of a heart or an entire heart concerning a given patient (a step S1). That is, volume data in time series (corresponding to at least one heart beat) of a desired observation region of a heart concerning a given patient is collected by using a two-dimensional array probe from a cardiac apex approach with a given time being determined as a reference.

[Generation of Tissue Motion Information: Step S2]

Then, each tissue motion information is generated (a step S2). That is, the movement vector processing unit 32 extracts a cardiac muscle region from volume data in a predetermined time phase in pieces of volume data corresponding to respective time phases of one heart beat or more constituting the collected time-series volume data group based on, e.g., an instruction from a user and temporally tracks the extracted local cardiac muscle region based on three-dimensional pattern matching processing, thereby calculating spatiotemporal movement vector information. The motion information arithmetic unit 33 three-dimensionally calculates heart wall motion information by using the calculated spatiotemporal movement vector information and generates a tissue motion information group constituted of three-dimensional motion information of one heart beat or more.

In this embodiment, it is assumed that the tissue motion information group concerning, e.g., radial strain is generated at the step S2 in order to give a concrete explanation. However, this is just an example, and the present invention is not restricted thereto. As the heart wall motion information which can be a generation target, there are, e.g., motion information concerning a change in a wall thickness direction (radial displacement, a radial displacement rate, radial strain, or a radial strain rate), motion information concerning a change in a longitudinal direction (e.g., a tangential direction of a long axis) (longitudinal displacement, a longitudinal displacement rate, longitudinal strain, or a longitudinal strain rate), motion information concerning a change in a circumferential direction (circumferential displacement, a circumferential displacement rate, circumferential strain, or a circumferential strain rate), motion information concerning an area centroid in a short-axis plane (rotation or a rotation rate), motion information as a difference in rotation between different short-axis planes (twist or a twist rate), motion information obtained by normalizing twist information based on a distance between short-axis planes (torsion or a torsion rate), motion information concerning a moving velocity (velocity), and others. Which one of the above-described pieces of heart wall motion information is to be generated is determined by an initial setting or a selecting operation from the operation unit 41. Furthermore, the movement vector processing unit 19 may generate the motion information separated into respective components, e.g., a wall thickness direction, a longitudinal direction, a circumferential direction, and others in accordance with a diagnostic purpose.

[Step 3: Segmentation of Tissue Motion Information in Each Time Phase]

Then, the control unit 31 segments the volume data concerning each time phase based on, e.g., an American Society of Echocardiography (ASE) 16-division method or an American Heart Association (AHA) 17-division method (a step S3). It is to be noted that a segmentation technique is not restricted in particular. For example, it is possible to utilize a technique which uses threshold value processing or a technique which estimates a positional correspondence relationship from a prepared heart model.

[Step S4: Generation of Various Motion Information Images including Support Information]

Subsequently, the image generation unit 21 uses the tissue motion information group to generate a time-series mapping image obtained by mapping the motion information (a step S4). For example, the image generation unit 21 uses the tissue motion information group to form a color code of the radial strain concerning a produced change in the wall thickness direction, and maps the color code onto a corresponding region of the cardiac muscle on a morphologic image to generate an MPR image, a polar mapping image, or a three-dimensional image in accordance with each time phase.

Further, the image generation unit 21 assigns a different color as the support information to each segment of the cardiac wall in each of the MPR image, the polar mapping image, and the three-dimensional image in accordance with a result of the segmentation executed at the step S3 and generates a frame representing a boundary between the respective segments.

[Step S5: Display of Various Images]

Then, the display unit 23 displays the MPR image, the polar mapping image, and the three-dimensional image with the tissue motion information mapped thereon together with the support information (i.e., color information assigned to each segment or frame information indicative of a boundary between the respective segments) which is generated at the step S4 (a step S5).

Figure 3:
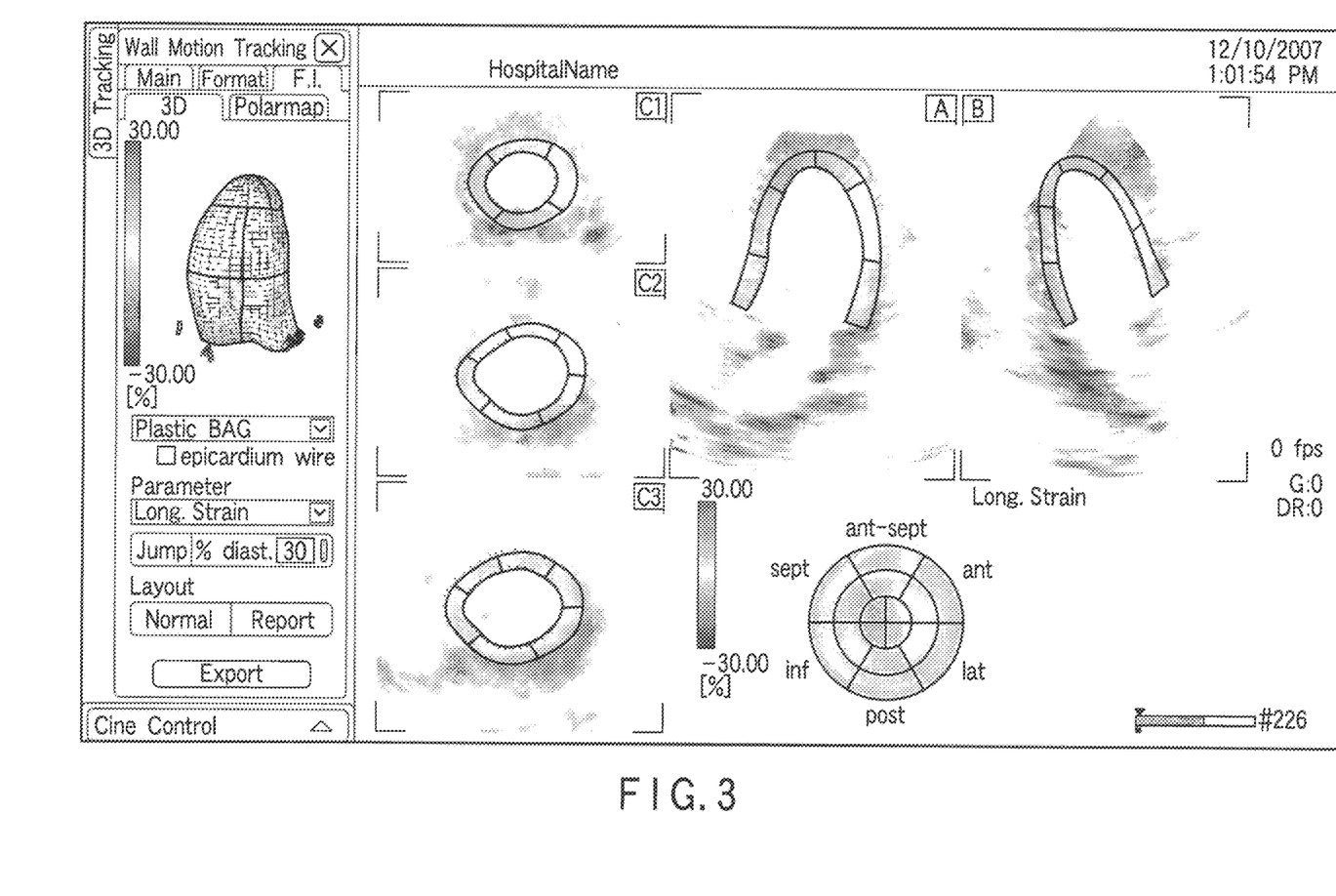
FIG. 3 is a view showing an example of display conformations of MPR images, a polar mapping image, and a three-dimensional image displayed at a step 5.

FIG. 3 is a view showing an example of display conformations of the MPR images, the polar mapping image, and the three-dimensional image displayed at this step. In the drawing, a stereoscopic image at an upper left is a three-dimensional image, an annular drawing at a lower right is a polar mapping image, and five two-dimensional cross sections on the right-hand side are MPR images (an A-plane image, a B-plane image, a C1-plane image, a C2-plane image, and a C3-plane image). Frames of various colors on each MPR image, the polar mapping image, and the three-dimensional image show segments conforming to ASE 16 segments in the form of frames, and specific colors are assigned to the respective 16 segments.

It is to be noted that the segments and shapes or positions of the segment frames fluctuate in time series in accordance with a result of tracking a myocardial wall. An operator can arbitrarily change a position or a shape (a size) of each segment frame by an operation from the operation unit 41 in order to facilitate observation of each segment. Further, display/non-display of the frame representing a boundary between the segments can be set in accordance with each segment. Therefore, when a position of a local region alone that the operator can see is displayed or when all the segments are set to non-display, the same display as that in the conventional example can be effected. Furthermore, when the operator specifies one or more segments, wall motion information (e.g., a time change curve of strain) of the specified segments alone can be displayed.

According to the above-described ultrasonic diagnostic apparatus, each MPR image, the polar mapping image, and the three-dimensional image having the tissue motion information mapped thereon are displayed together with the information of a color assigned to each segment or the information of a frame representing a boundary between the respective segments. Therefore, an observer such as a doctor can rapidly and readily grasp a correspondence relationship between positions of each MPR image, the polar mapping image, and the three-dimensional image based on a correspondence relationship between colors of the respective displayed images or positions/shapes of the frames.

(Modification 1)

A modification of the ultrasonic diagnostic apparatus 1 according to this embodiment will now be explained. An ultrasonic diagnostic apparatus 1 according to this modification sets and displays a marker which indicates a desired local position as support information that is used to rapidly and easily visually confirm a relative positional correspondence relationship between each MPR image, a polar map image, and a three-dimensional image in a tissue motion information display function.

For example, a situation where a desired region in various images displayed at the step S5 is specified by an operator through an operation unit 41. In this case, a control unit 31 sets a position corresponding to the region specified by the operator on volume data in each time phase. An image generation unit 21 sets a marker indicating the region specified by the operator on each MPR image, a polar mapping image, and a three-dimensional image based on a judgment result. A display unit 23 displays the MPR image, the polar mapping image, and the three-dimensional image each having the maker as support information superimposed thereon in a predetermined conformation.

Figure 4:
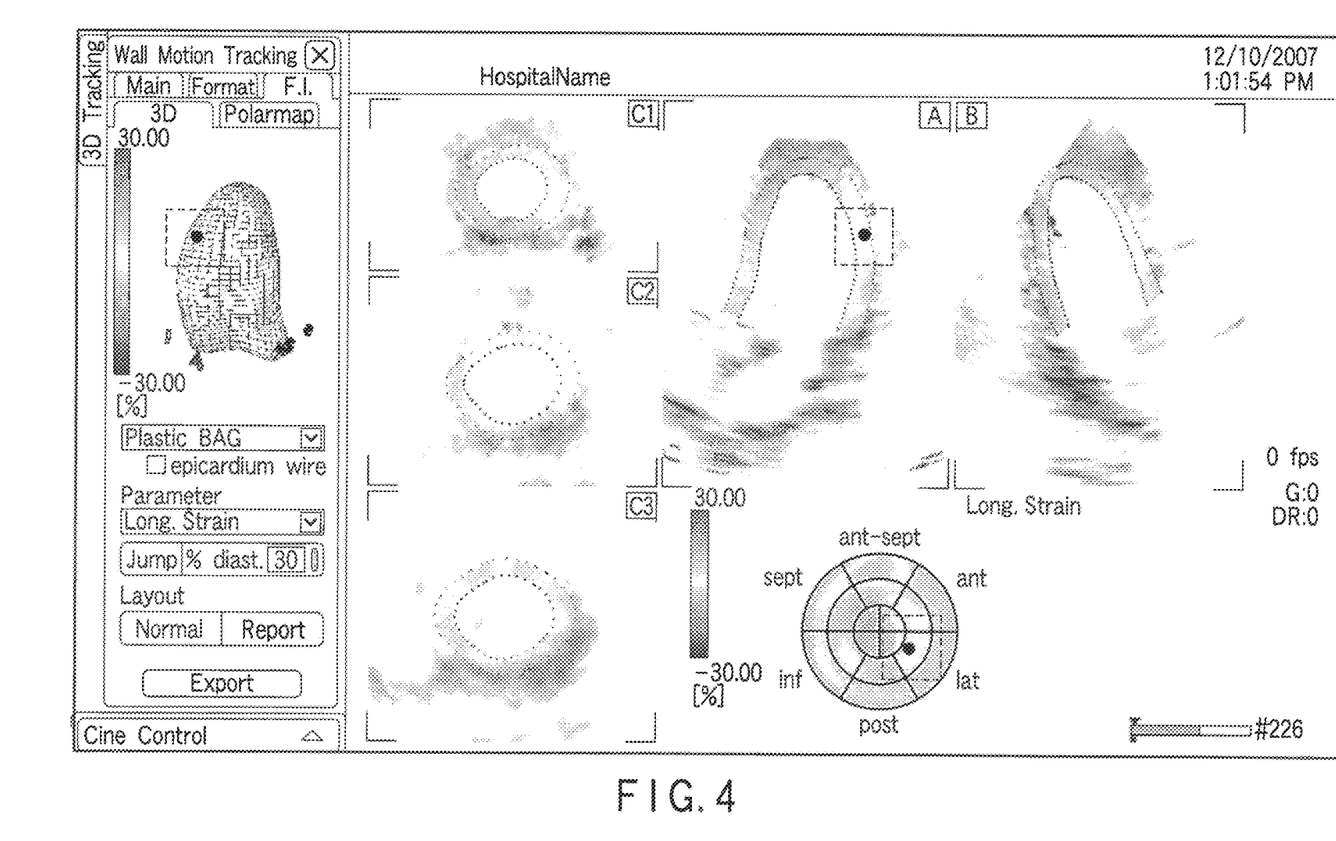
FIG. 4 is a view showing an example of the MPR images, the polar mapping image, and the three-dimensional image having markers set thereon.

FIG. 4 is a view showing an example of the MPR images, the polar mapping image, and the three-dimensional image having the marker set thereon. The marker set on each image is indicative of the same region on a heart wall. An observer such as a doctor can rapidly and easily grasp a correspondence relationship between positions of the MPR images, the polar mapping image, and the three-dimensional image by observing a marker position on each displayed image.

It is to be noted that the drawing shows the example where segment frames are not displayed in order to emphasize the marker display. However, the present invention is not restricted to this example, and the segment frames can be displayed together with the markers. Furthermore, each marker fluctuates in time series in accordance with a result of tracking a cardiac muscle wall. An operator can arbitrarily change a position or a size of each marker. Moreover, a plurality of markers can be set in one segment or can be set over a plurality of segments. Display/non-display can be set in accordance with each marker. Additionally, when the operator specifies one or more markers, wall motion information (e.g., a time change curve of strain) of specified segments alone can be displayed.

(Modification 2)

Another modification of the ultrasonic diagnostic apparatus according to this embodiment will now be described. When the marker according to Modification 1 is set or changed on the polar mapping image or the three-dimensional image, a position corresponding to the set or changed marker is not present on the MPR image in some cases. An ultrasonic diagnostic apparatus according to this modification generates and displays an MPR image always including a position corresponding to the set or changed marker by automatically adjusting a position of an MPR cross section in such a case.

Figure 5:
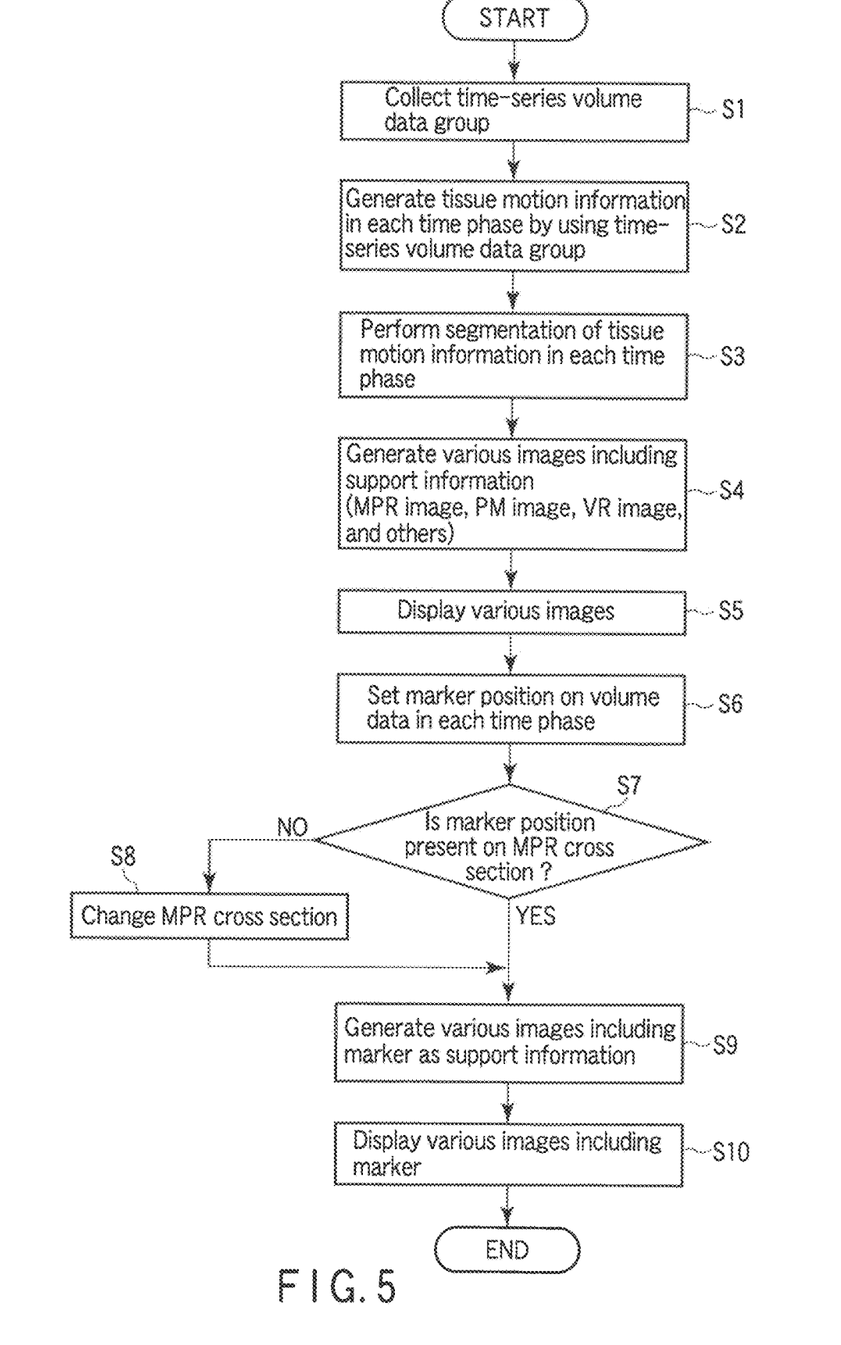
FIG. 5 is a flowchart showing a flow of the tissue motion information display processing according to a modification.

FIG. 5 is a flowchart showing a flow of a tissue motion information display processing according to this modification. In this drawing, for example, it is assumed that an operator specifies a desired marker set position with respect to a polar mapping image displayed at the step S5 through an operation unit 41. In this case, a control unit 31 sets a position corresponding to a region specified by an operator on volume data in each time phase (a step S16). Further, the control unit 31 judges whether a determined position is present on any one of current MPR images (a step S17).

When it is determined that the determined position is not present on all MPR images as a result of the judgment, the control unit 31 changes a position of any MPR cross section to include a maker position based on the marker position set on the volume data. For example, when a coordinate of the set marker is closer to a plane A than a plane B on the volume data, the control unit 31 translates the plane A to be changed to a cross section including the marker coordinate.

Furthermore, the control unit 31 changes a position of the plane B in such a manner that an angle or a distance from the plane A becomes equal to that in a state before changing the plane A.

Moreover, this operation can be likewise applied to three cross sections C (C1, C2, and C3) as the MPR images. For example, when the coordinate of the marker on a polar map is closest to the plane C3, the control unit 31 first translates the plane C3 to be changed to a cross section including the marker coordinate. Additionally, the control unit 31 changes each of positions of the remaining planes C1 and C2 in such a manner that an angle or a distance from the plane C3 remains the same as a state before changing the plane A.

An image generation unit 21 generates MPR images, a polar map image, a three-dimensional image including markers as support information based on the changed MPR cross section (a step S19). A display unit 23 displays the MPR images, the polar mapping image, and the three-dimensional image having the markers superimposed thereon (a step S20).

According to the above-described configuration, the marker set at an arbitrary position can be placed on all of the MPR images, the polar mapping image, and the three-dimensional image to rapidly and easily visually confirm and observe a positional correspondence relationship.

Compared with a conventional polar mapping image (e.g., a polar mapping image acquired by a nuclear medicinal diagnostic apparatus), a conventional polar mapping image acquired by the present nuclear medicinal diagnostic apparatus is intended to visualize the entire left ventricle as one image. In contrast, the present ultrasonic diagnostic apparatus merely sets a marker at a desirable position on one of an MPR image, a polar mapping image and a three-dimensional image, and by so doing, the corresponding positions on the remaining two images are automatically set. In other words, the present ultrasonic diagnostic apparatus is intended to clarify the correspondence of a desirable position among the MPR image, polar mapping image and three-dimensional image. Therefore, the present ultrasonic diagnostic apparatus displays which position on the polar mapping image corresponds to a designated point on either the MPR image or the three-dimensional image, and also displays which position on the MPR image or the three-dimensional image corresponds to a local position designated on the polar mapping image. The observer can observe the images while visually recognizing the positional correspondence among the three images quickly and easily. As can be understood from this, a polar mapping image acquired by the present ultrasonic diagnostic apparatus is not displayed merely as an image, like a polar mapping image acquired by a conventional nuclear medicinal diagnostic apparatus; it is presented as an image retaining information on the correspondence among the polar mapping image, MPR image and three-dimensional image.

It is to be noted that the present invention is not restricted to the foregoing embodiment as it is and constituent elements can be modified and realized without departing from the scope of the invention on an embodying stage. For example, each function according to the embodiment can be also realized by installing a program that executes the processing in a computer such as a work station and expanding this program on a memory. At this time, the program that allows the computer to carry out a corresponding technique can be stored in a recording medium such as a magnetic disk (e.g., a floppy (a registered trademark) disk or a hard disk), an optical disk (e.g., a CD-ROM or a DVD), or a semiconductor memory to be distributed.

Additionally, appropriately combining a plurality of constituent elements disclosed in the foregoing embodiment enables forming various inventions. For example, some of all constituent elements disclosed in the embodiment may be eliminated. Further, constituent elements in different embodiments may be appropriately combined.

What is claimed is:

1. An ultrasonic image display apparatus, comprising:
   a memory to store time series image data of a region including a tissue in an object, the time series image data being generated based on outputs from an ultrasound probe; and
   processing circuitry configured to:
   calculate tissue motion information of the tissue for each of a plurality of time phases based on the time series image data by a tissue tracking process;
   generate three-dimensional images and polar mapping images based on the same tissue motion information calculated by the tissue tracking process, the three-dimensional images and the polar mapping images including color information based on the calculated tissue motion information, and including frame information indicative of a boundary between segments; and wherein the three-dimensional images are time series three-dimensional images and the polar mapping images are time series polar mapping images, and
   cause a display to display the three-dimensional images further including support information, and the polar mapping images further including the support information, simultaneously, the support information representing a correspondence relationship between a segment of the three-dimensional images and a segment of the polar mapping images, the three-dimensional images and the polar mapping images being generated by the same tissue motion information calculated by the tissue tracking process; wherein the processing circuitry is further configured to cause the display to display the time series three-dimensional images and the time series polar mapping images sequentially and synchronously.

2. The apparatus according to claim 1, wherein the processing circuitry is further configured to generate a marker as the support information.

3. A medical image diagnostic apparatus, comprising:
   processing circuitry configured to:
   generate time series image data of a region including a tissue in an object based on outputs from an ultrasound probe;
   calculate tissue motion information of the tissue for each of a plurality of time phases based on the time series image data by a tissue tracking process;
   generate three-dimensional images and polar mapping images based on the same tissue motion information calculated by the tissue tracking process, the three-dimensional images and the polar mapping images including color information based on the calculated tissue motion information, and including frame information indicative of a boundary between segments; and wherein the three-dimensional images are time series three-dimensional images and the polar mapping images are time series polar mapping images, and
   cause a display to display the three-dimensional images further including support information, and the polar mapping images further including the support information, simultaneously, the support information representing a correspondence relationship between a segment of the three-dimensional images and a segment of the polar mapping images, the three-dimensional images and the polar mapping images being generated by the same tissue motion information calculated by the tissue tracking process; wherein the processing circuitry is further configured to cause the display to display the time series three-dimensional images and the time series polar mapping images sequentially and synchronously.

4. The apparatus according to claim 3, wherein the support information represents correspondence relationships between segments of the three-dimensional images the polar mapping images.

5. The apparatus according to claim 3, wherein the support information displayed on each segment of a three-dimensional image included in the three-dimensional images is different from each other.

6. The apparatus according to claim 3, wherein the image data is volume data of a three-dimensional region including the tissue.

7. The apparatus according to claim 3, wherein the processing circuitry is further configured to generate a marker as the support information.

8. The apparatus according to claim 3, wherein the processing circuitry is further configured to:
generate time series MPR images based on the time series image data, and
superimpose the support information on the time series MPR images.

9. A processing method of a medical image, comprising:
generating time series image data of a region including a tissue in an object based on outputs from an ultrasound probe;
calculating tissue motion information of the tissue for each of a plurality of time phases based on the time series image data by a tissue tracking process;
generating three-dimensional images and polar mapping images based on the same tissue motion information calculated by the tissue tracking process, the three-dimensional images and the polar mapping images including color information based on the calculated tissue motion information, and including frame information indicative of a boundary between segments; and
wherein the three-dimensional images are time series three-dimensional images and the polar mapping images are time series polar mapping images, and
causing a display to display the three-dimensional images further including support information, and the polar mapping images further including the support information, simultaneously, the support information representing a correspondence relationship between a segment of the three-dimensional images and a segment of the polar mapping images, the three-dimensional images and the polar mapping images being generated by the same tissue motion information calculated by the tissue tracking process; wherein the processing circuitry is further configured to cause the display to display the time series three-dimensional images and the time series polar mapping images sequentially and synchronously.

10. The processing method of claim 9, wherein the causing step includes causing the display to display the three-dimensional images and polar mapping images, each with the support information, wherein unique support information is assigned to respective segments.

11. The processing method of claim 9, wherein the causing step includes causing the display to display the three-dimensional images and polar mapping images, each with the support information, wherein the support information is not based on the tissue motion information.

12. An ultrasonic image display apparatus, comprising:
a memory to store time series image data of a region including a tissue in an object, the time series image data being generated based on outputs from an ultrasound probe; and
processing circuitry configured to:
calculate tissue motion information of the tissue for each of a plurality of time phases based on the time series image data by a tissue tracking process;
generate three-dimensional images and polar mapping images based on the same tissue motion information calculated by the tissue tracking process, the three-dimensional images and the polar mapping images including color information based on the calculated tissue motion information, and including frame information indicative of a boundary between segments, the color information and the frame information representing a correspondence relationship between a segment of the three-dimensional images and a segment of the polar mapping images, wherein the three-dimensional images are time series three-dimensional images and the polar mapping images are time series polar mapping images; and
cause a display to display the time series three-dimensional images and the time series polar mapping images sequentially and synchronously.

13. The ultrasonic image display apparatus according to claim 12, wherein the tissue includes a part of a heart.

14. The ultrasonic image display apparatus according to claim 12, wherein the same tissue motion information includes wall motion information.

15. The ultrasonic image display apparatus according to claim 14, wherein the wall motion information includes strain information.

16. The ultrasonic image display apparatus according to claim 14, wherein the wall motion information includes displacement information.

17. The ultrasonic image display apparatus according to claim 12, the processing circuitry is configured to cause the display to further display a time change curve of the wall motion information.

18. The ultrasonic image display apparatus according to claim 15, the processing circuitry is configured to cause the display to further display a time change curve of the strain information.

19. The ultrasonic image display apparatus according to claim 12, wherein the processing circuitry is configured to move the boundary displayed on three-dimensional images based on the calculated tissue motion information.

20. The ultrasonic image display apparatus according to claim 12, wherein the processing circuitry is configured to cause the display to further display a first marker on the time series three-dimensional images and a second marker on the time series polar mapping images, a position of the first marker corresponding to a position of the second marker.

21. The ultrasonic image display apparatus according to claim 12, wherein the processing circuitry is configured to cause the display to display the time series three-dimensional images and the time series polar mapping images in different display positions in a horizontal direction.

* * * * *